United States Patent
Faunce

[11] 3,986,261
[45] Oct. 19, 1976

[54] METHOD AND APPARATUS FOR RESTORING BADLY DISCOLORED, FRACTURED OR CARIOUSLY INVOLVED TEETH

[76] Inventor: Frank R. Faunce, 1307 Wilcrest Drive, Apt. 237, Houston, Tex. 77025

[22] Filed: Dec. 5, 1973

[21] Appl. No.: 421,846

[52] U.S. Cl. .................................. 32/12; 32/15
[51] Int. Cl.² ................................. A61C 5/08
[58] Field of Search .............. 32/15, 1, 5, 6, 7, 8, 32/71, 12

[56] References Cited
UNITED STATES PATENTS

| | | | |
|---|---|---|---|
| 3,004,343 | 10/1961 | Rydin | 32/13 |
| 3,469,317 | 9/1969 | Jarby | 32/15 |
| 3,503,128 | 3/1970 | Boyd et al. | 32/15 |

FOREIGN PATENTS OR APPLICATIONS

| | | | |
|---|---|---|---|
| 1,122,220 | 1/1962 | Germany | 32/15 |
| 2,008,781 | 12/1971 | Germany | 32/12 |

*Primary Examiner*—Louis G. Mancene
*Assistant Examiner*—Jack Q. Lever

[57] ABSTRACT

A method and apparatus for restoring badly discolored, fractured or cariously involved teeth by etching desirable parts of the enamel surface of the tooth and by adhering to the tooth a properly colored polymerized, preformed plastic facing that has a pleasing cosmetic appearance or corresponds to the coloring of adjacent teeth as desired. The etched surface of the tooth, the inside surface of the facing material and the exposed surface of the facing material including the joint between the facing material and the enamel of the tooth are coated with a controlled curing dental adhesive material that may be selectively cured in place, such as by ultra-violet activation. The voids between the tooth and the facing material may be filled with a controlled curing dental filler material that may also be molded about the joint between the tooth enamel and the facing material. The dental filler material may also be of the type that is cured in place such as by curing following ultra-violet activation. Facings bonded to the enamel of abutment teeth may be employed for support of pontics without necessitating preparation of abutment teeth with bridgework support crowns. Connected facings may also be employed for periodontic splinting.

27 Claims, 8 Drawing Figures

METHOD AND APPARATUS FOR RESTORING BADLY DISCOLORED, FRACTURED OR CARIOUSLY INVOLVED TEETH

FIELD OF THE INVENTION

This invention relates generally to both cosmetic and structural restoration of teeth such as teeth that are badly discolored, teeth that have been fractured or teeth that have become cariously involved. More particularly, the invention relates to restoration of teeth by means of laminar overlay where a desirably colored preformed facing of fully polymerized plastic material may be bonded to the enamel of the tooth to provide teeth of pleasing cosmetic appearance or to provide a fully restored properly shaped and properly colored tooth restoration. The invention also relates to laminar support means for pontics in dental bridgework and for laminar splinting of periodontically involved teeth.

BACKGROUND OF THE INVENTION

Many phenomenon occur that have the adverse effect of causing teeth to become badly discolored and in many cases, teeth of children or adults become discolored during the formative period or later. Some of the causes of tooth discoloration are pharmaceutical discoloration that occurs when children are required to take certain drugs. Certain drugs have been known to cause the teeth of children to have various shades of yellow or brown if such drugs are taken before the permanent teeth of a child erupt. Discoloration also occurs due to the diet of persons that live in certain parts of the world, largely due to the minerals that are ingested along with the water that is consumed. The dental patient may also have a hyperplastic condition where the enamel of the teeth does not fully develop, causing the teeth to become easily discolored. A hyperplastic condition may also be evident, where the teeth of the patient may have an excess of mineral salt deposit that causes the teeth of the patient to have white spots. (Metabolic diseases such as those releasing bile pigments or hemorrhagic disturbances that release blood pigments may cause a discoloration of teeth. Bacteria frequently cause staining of teeth, e.g., green stain or tobacco stain.)

Thus far, there has been no effective method of treating discolored teeth in order to give them a pleasing cosmetic appearance. In the past, the only effective way the cosmetic appearance of teeth could be improved is for the teeth to be capped with plastic or porcelain crowns. This is a very expensive and time consuming procedure and the costs involved have the effect of eliminating cosmetic capping for all but a few patients. Decorative inlays have also been employed in the past but the difficulty of bonding materials to the enamel of teeth effectively prevent this procedure from being commercially feasible in the practice of dentistry.

When teeth become fractured or cariously involved, it frequently becomes necessary to restore the teeth to their proper shape and appearance to promote proper incisive and masticatory function and for cosmetic purposes. If a tooth has become fractured and restoration is desirable, in the past restoration has been accomplished by application of crowns to the teeth, which crowns have been composed of metal materials such as gold and plastic materials, such as methyl methacrylate polymer. An acceptable restoration has been accomplished in the past by application of jacket crowns to the teeth and by application of porcelain that is fused to gold crowns. These crowns typically involve a great deal of expense and also involve a great deal of dental chair time for application. For example, restoration of teeth by application of gold crowns may cost in the order of $200 to $225 and may require as much as three hours chair time in order to complete the installation of each crown.

A primary disadvantage in the application of crown restorations to teeth is the requirement that the tooth be preshaped to the drastic degree in order that the crown may be properly applied thereto. For proper application of crowns it is necessary that the crown and the tooth be prepared in order to achieve resistance as retention of the crown. The crown, in a proper application, is retained in position on the tooth by proper fitting to provide resistance and retention and the presence of crown cement between the prepared tooth and the crown is primarily for the purpose of filling any voids that might exist and thereby prevent debris from becoming deposited in the voids between the crown and the prepared tooth. The cement disposed between the crown and the tooth, although providing a gripping function to some degree, does not provide the primary gripping function that retains the crown in physical assembly with a tooth structure. One reason for this is the fact that the cements that have been used in the past for cementing crowns to prepared teeth, during crown restoration of the teeth, is a water soluble material and in time, if a crack or fissure is present between the tooth and the crown, saliva will penetrate the joint between the crown and the tooth and dissolve the cement. If proper resistance and retention were not provided between the crown and the tooth, the crown would become separated quite readily from the tooth structure.

A more recently utilized method of tooth restoration has been utilized that is effective in restoration of fractured teeth as well as teeth that have developed caries. After etching of the teeth with an acid solution, such as 50 to 75 percent phosphoric acid or citric acid for a short period of time, for the purpose of removing mineral salts from the enamel surface and creating spaces or "micro pores" in the enamel where the mineral salts have been dissolved by the acid, a dental sealant material may be applied to the acid prepared enamel surface which sealant enters the micro pores and when polymerized, forms an intimate mechanical bond with the enamel surface of the tooth. The dental sealer material may be of the type that is produced by the reaction product of Bisphenol A and Glycidyl Methacrylate such as a product manufactured and sold under the trademark of Nuva-Seal by the Caulk Division of Dentsply International, Inc. of Millford, Delaware. The sealant product, referred to as "Nuva-Seal," is activated by Benzoin methyl ether catalyst prior to application thereof to a tooth surface and is polymerized after application to the surface by exposure to ultra-violet light.

After application of the sealant material to the prepared enamel surface of the tooth, a dental filler material may be applied to the prepared and sealed surface and may be shaped essentially to the original configuration of the tooth with a plastic shaping instrument. The dental filler material may also be of a character that is based upon the reaction product of Bisphenol A and Glycidyl Methacrylate which is also activated by Benzoin methyl ether catalyst and selectively polymerized by exposure to ultra-violet light. A dental filler material that is suitable for this purpose is sold by the Caulk Division of Dentsply International, Inc. under the trademark "Nuva-Fil." This material will not become polymerized until it is selectively exposed to ultra-violet light. The material, therefore, may be worked for whatever period of time is necessary to properly shape the tooth restoration to its desired physical characteristics and polymerization will occur in a few seconds time after application of ultra-violet light to the shaped material. After the dental filler material has been shaped and polymerized, the outer surface of the filler material and a portion of the exposed enamel at the marginal portions of the filler material may be finally shaped with appropriate sanding or grinding instruments and a coating of dental sealer material may be then applied to desirable portions of the restored tooth and may be subsequently polymerized by application of ultra-violet light.

Although excellent tooth restorations may be accomplished by the above noted use of ultra-violet light polymerized dental sealer and filler material, it is very difficult to achieve precise color matching of the restored tooth to the color of a adjacent teeth. The restoration process therefore is often less than desirable from aesthetic standpoint. The dental filler and sealer material is commercially produced in a few different shades in order that color matching may be accomplished as nearly as possible, but it is well known that wide variation in color and tooth appearance is found in the teeth of dental patients. It is virtually impossible to select from the few shades of materials that are available a material that is capable of precisely matching with the color and appearance of adjacent tooth if color matching is indeed desirable.

In many cases, it is not desirable to match the tooth restoration material with the adjacent teeth, especially when the patients natural teeth have become discolored to the point that the cosmetic appearance is undesirable.

In the event one or more teeth should be missing, it is typically necessary to employ a dental bridge wherein a dental prothesis is connected to teeth adjacent the opening produced by the missing tooth and an artificial tooth or pontic forming a part of the prothesis is supported in the space to prevent migration of the adjacent teeth. In view of the fact that bridge work may not be supported by the enamel of abutment teeth adjacent an opening, it is typically necessary to provide the adjacent teeth with crown restorations even though these teeth may be perfectly normal. The crowns may be provided with appropriate means for physical attachment of the bridge work in order to support the bridge work prothesis. It is, of course, undesirable to provide crown restorations for perfectly normal teeth, although in some cases this is necessary to avoid the problems that may occur by migration of teeth by absence of one or more of the patient's permanent teeth. It is desirable, therefore, to provide means for preparing the abutment teeth adjacent an opening caused by a missing tooth or teeth with means for positively securing a prothesis bridge work in place without necessitating the tooth preparation that is necessitated by application of bridge work support crowns.

It is therefore a primary object of the present invention to provide a novel method of providing teeth of a patient with a laminar overlay for the purpose of providing a pleasing cosmetic appearance to the teeth.

It is an even further object of the present invention to provide a novel preformed fully polymerized laminant that may be effectively bonded to the enamel surface of a patient's teeth for the purpose of improving the cosmetic appearance of the teeth and for the purpose of providing efficient low cost, cosmetically pleasing tooth restorations.

It is also an object of the present invention to provide a method of tooth restoration for cosmetic or functional purposes that may be simply and efficiently accomplished with little or no alteration of the physical characteristics of the tooth being treated.

It is another object of the present invention to provide a novel method of cosmetically or functionally restoring teeth wherein the entire restoration process may be accomplished in a short period of time without necessitating use of anesthesia.

It is an even further object of the present invention to provide a novel method of restoring fractured or cariously involved teeth that may be accomplished effectively through the use of low cost materials to provide a restoration having the exceptional quality and a pleasing cosmetic appearance.

Among the several objects of the present invention is noted the contemplation of a novel method of restoring fractured or cariously involved teeth wherein facings composed of a suitable plastic material may be bonded to the enamel of a tooth to be restored, which plastic material may, if desirable, have the external appearance of the patient's natural teeth and which material will also match the functional characteristics of the patient's teeth.

It is another important object of the present invention to provide a novel method of restoring teeth wherein preformed plastic facings may be employed, which facings may be marked with checks, stains, etc. to match the coloring and characteristics of the patient's adjacent teeth.

It is also an object of the present invention to provide a novel method of restoring teeth wherein a plastic facing may be applied to a tooth to be restored and may be inspected for physical shape and cosmetic appearance prior to permanent bonding of the plastic facing to the tooth's structure and if not satisfactory, the facing may be simply and efficiently removed and another substituted therefor in order to provide a pleasing cosmetic appearance. After the dentist, and perhaps also the patient, has approved the cosmetic appearance and physical shape of the restored tooth, the unpolymerized portion of the restoration may be selectively polymerized to complete the restoration process.

It is also an important object of the present invention to provide a novel method of restoring teeth wherein plastic material utilized in the restoration process may be selectively polymerized in place to provide a hard and durable restoration that, with responable dental care, will last for very long periods of time.

It is another feature of the present invention to provide anchor means for dental bridge work prothesis without necessitating grinding away of abutment teeth adjacent to an opening caused by a missing tooth or teeth that otherwise must be necessary in order to provide prothesis anchor crowns on the abutment teeth supporting the bridge work.

It is an even further feature of the present invention a method of restoring or otherwise treating a patient's teeth in order to provide for periodontal splinting of a patient's teeth.

It is also an object of the present invention to provide a method of restoring teeth, which restoration process if unsatisfactory when completed or, if such restoration becomes undesirable subsequent to a completion of the process, may be completely and efficiently removed from the tooth or teeth so involved, thereby returning the teeth to the original pretreatment condition thereof.

Other and further objects, advantages and features of the present invention will become apparent to one skilled in the art upon consideration hereof. The form of the invention, which will now be described in detail, illustrates the general principles of the invention, but it is to be understood that this detailed description is not to be taken as limiting the scope of the present invention.

SUMMARY OF THE INVENTION

A preferred embodiment of the present invention may conveniently take a form of a method and materials for restoring badly discolored, fractured or cariously involved teeth, wherein the method includes selection of a preformed fully polymerized plastic lamination or facing that may be composed of a suitable plastic material and which may be selected according to color and physical appearance in order to provide teeth of pleasing aesthetic appearance. The preformed facing or lamination may be further modified by shaping or grinding in order to fit the configuration of the tooth being restored as precisely as possible. After the color, shape and physical characteristics of the tooth have been matched as desired and after the facing has been preshaped to fit the tooth being restored, the enamel surface of the tooth to be restored may be etched with an acid material, such as a solution of 75 percent phosphoric acid, for a sufficient period of time to prepare the appropriate enamel surface of the tooth for reception of a dental sealant material that may be polymerized in place. The inside surface of a plastic facing to be secured to the tooth to be restored may also be coated with a thin coating of the same dental sealant material which material may be polymerized in any suitable manner. A coating of a dental filler material that may be subsequently polymerized may then be applied to the tooth to be restored or to the facing to be bonded to the tooth and the facing may be applied to the tooth in such manner as to squeeze out any excess dental filler material, thus filling all of the voids between the tooth and the facing with the filler material. A small amount of the dental material existing at the marginal edges of the facing may be smoothed about the marginal edges in order to provide a smooth contour at the joint between the edges of the facing and the enamel surface of the tooth. After inspection of the tooth to insure that the color and physical characteristics of the facing exactly match the color and physical characteristics of adjacent teeth, the filler material may be selectively polymerized in place, where it is rendered from a paste or putty-like consistency to a hard porcelain-like durable consistency. The dental sealant material and the dental filler material may both be composed of a compound that will remain unpolymerized or uncured for a relatively indefinite period of time and which may be subsequently polymerized in a few seconds time by application of ultra-violet light thereto. The dental filler material may also be of the type that is premixed prior to application thereof to the teeth of the patient and which is allowed to become polymerized in place following a predetermined curing period.

BRIEF DESCRIPTION OF THE DRAWINGS

So that the manner in which the above recited features, advantages and objects of the present invention, as well as others, which will become apparent, are attained and can be understood in detail, more particular description of the invention, briefly summarized above, may be had by the reference to the embodiments thereof which are illustrated in the appended drawings, which drawings form a part of this specification.

It is to be noted however that the appended drawings illustrate only typical tooth restorations that are made possible by employment of the method and materials set forth herein and are therefore not to be considered limiting of its scope, for the invention may admit to other equally effective embodiments.

In the Drawings.

DESCRIPTION OF PREFERRED EMBODIMENTS

Figure 1:
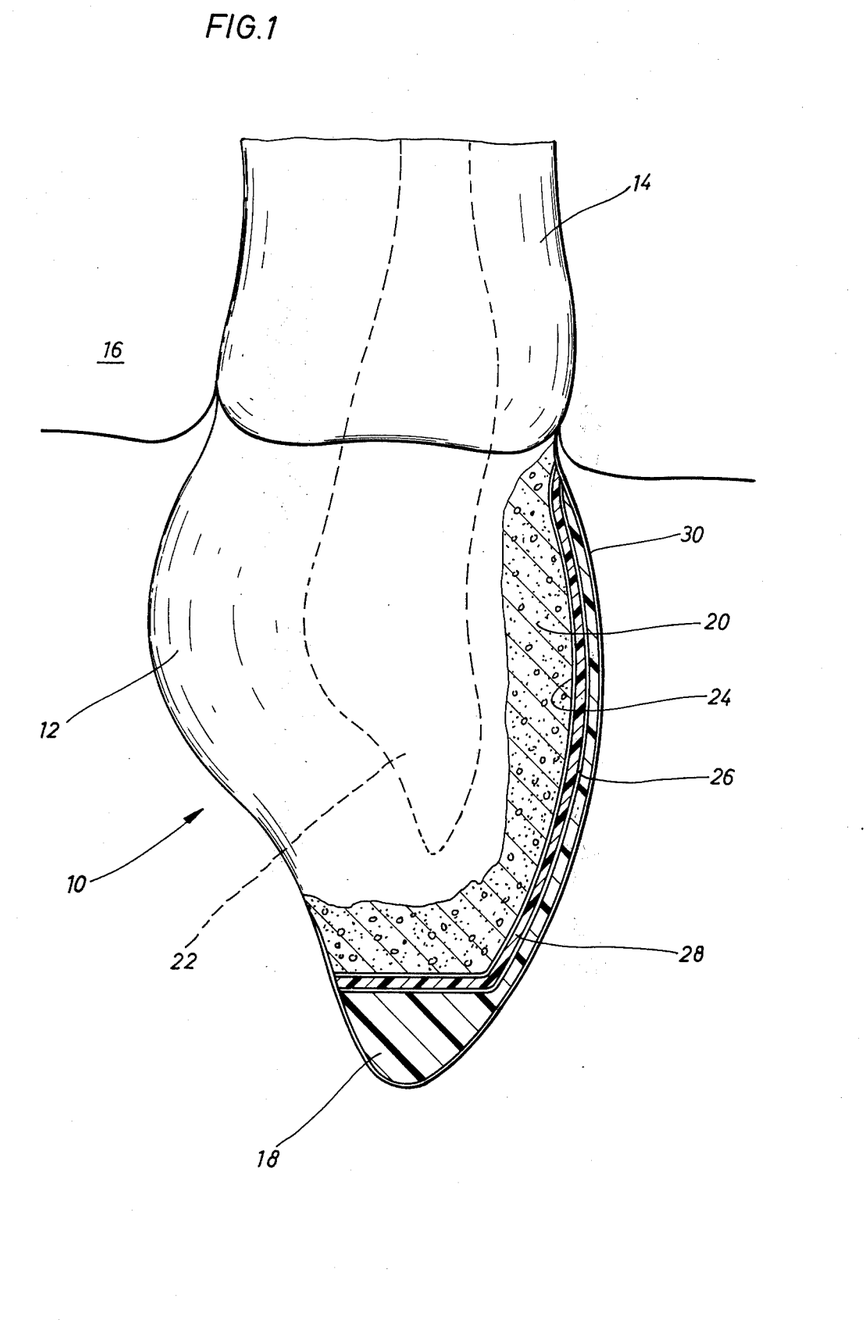
FIG. 1 is a side elevational view of an anterior tooth having a portion of the enamel thereof shown in section and showing a preformed plastic facing that has been applied to the labial and incisal portions of the tooth in accordance with the present method.

Now referring to the drawings and first to FIG. 1 a tooth structure is illustrated generally at 10, which tooth is an anterior incisor having a fractured incisal portion. The exposed crown portion 12 of the tooth is shown as having a laminar plastic restoration applied thereto which laminar restoration also includes a lower incisal portion to restore the fracture of the tooth. A portion of the root 14 of the tooth is shown positioned relative to gum tissue surrounded thereabout.

Assuming that the tooth 10 has a fractured incisal portion as shown and perhaps that the labial surface of the enamel is badly discolored or that perhaps the incisal or labial lingual or proximal portions of the tooth may be cariously involved to the point that partial restoration is desirable, according to the method of the present invention, a restoration technique may be employed wherein a thin sheet-like preformed plastic facing 18 may be bonded to the enamel portion 20 of the tooth structure. It is not necessary, as in the past, to grind away the tooth structure and expose the dentin shown in broken line at 22 unless the presence of caries necessitates such activity. In fact, it is not necessary to remove any major portion of the tooth structure to achieve complete restoration of the tooth.

It may be desirable to prepare a very small portion of the exposed surface of the enamel in order to remove undesirable mineral deposits that might interfere with the bonding process. This may be accomplished by very light sanding. Desired portions of the exposed enamel then may be prepared for bonding by application of a suitable acid material for a short period of time. This is known as acid etching, a process that creates spaces or "micropores" within the surface layer of enamel which will allow a dental sealant material to penetrate into the surface of the enamel itself and establish an efficient mechanical interlocking bond with the enamel. As the tooth is etched, projections, which may be referred to as "rods" or "tags" are developed which increase the physical bonding of the sealant to the tooth structure. The employment of acidic conditioning agents has an effect on the tooth enamel that removes at least a portion of the mineral salts from the enamel surface to a very shallow depth, i.e., in the order of 25 microns, thereby creating spaces or micropores in the enamel where the mineral salts have been dissolved. Etching of the tooth enamel, although initially creating a dull appearance on the enamel surface does not constitute permanent alteration of the enamel surface of the tooth. In fact, areas of enamel surface that are etched, if not covered by a coating of dental sealant material, will return to its normal translucency within a few days. It is theorized that acid etched enamel is remineralized by the disposition of calcium phosphate salts from the saliva. Other than the creation of a superficial etch, there appears to be no detrimental effect to the tooth tissue.

After acid etching of desirable portions of the enamel of the tooth, the acid etched enamel is maintained clear of any material such as water, oil, saliva that might interfere with the bonding process and a dental sealant material is applied thereto and is allowed to subsequently become catalyzed in place in order to seal the micropores that have been established by the etching process and to establish the physical surface to which a plastic lamination may be effectively bonded. Although the dental sealant material may take any suitable form within the spirit and scope of the present invention, it may be desirable to employ a dental sealant material such as that sold under the trademark Nuva-Seal by the Caulk Division of Dentsply International, Inc., mentioned hereinabove, and referred to hereinafter merely as sealant. The sealant is a very "wet" material that will readily penetrate the minute interstices or micropores that are developed on the enamel surface during the etching process. After application of the coating 24 to the prepared surface portions of the tooth enamel, a coating 26 of similar sealant material may be applied to the inside surface portion of the preformed plastic facing 18. The surface coatings of both the tooth and the facing may be then polymerized, which in the case of Nuva-Seal dental sealant is accomplished by means of exposure to ultra-violet light after having been previously activated by Benzoin methyl ether catalyst in the manner discussed above.

After the coatings 24 and 26 of the enamel and facing respectively, have become catalyzed, hardening the sealant material to a porcelain-like quality, a quantity 28 of a dental filler material may be applied either to the facing 18 or to the prepared and coated portion 24 of the tooth enamel and the plastic facing material may be brought into intimate contact with the tooth structure. It is desirable that the dental filler material be capable of controlled polymerization or curing in order that it may be inspected for physical shape and cosmetic appearance and approved before it is permanently bonded to the tooth structure. If during inspection, it is found that the preformed facing 18 is of undesirable color characteristics and does not precisely match with adjacent teeth or with exposed portions of the tooth being restored, it will be desirable to simply remove the preformed facing and substitute a facing of proper color and shape. Ordinarily, the facing material will be emplaced prior to application of coatings to the tooth structure in order that the color characteristics of the facing may be precisely matched with adjacent teeth.

After the preformed facing has been installed in proper position, it is tightly pressed to the tooth structure and excessive dental filler material is squeezed out about the marginal edges of the facing material. All of the voids between the external tooth structure and the internal surface of the facing material will be filled with the dental filler material thereby establishing proper structural integrity of the restoration. Most of the excessive filler material that has been squeezed from between the tooth and facing is removed and a small portion of the filler material may be molded about the joint established between the marginal edge of the facing material and the adjacent enamel portion of the tooth. The marginal edges of the preformed facing that engage the enamel surface of the tooth to be restored will be of very thin knifelike configuration to define an edge margin that blends smoothly to the enamel surface of the tooth. After this has been done and the physical shape of the restoration has been approved, the dental filler material may be polymerized, thereby causing it to harden to a very hard porcelain-like characteristic.

Following polymerization of the dental filler material, the preformed plastic facing and the tooth enamel surface adjacent the marginal edges of the facing may be sanded or ground lightly in order to ensure a smooth and continuous restored tooth surface. Restoration then may be completed by application of a coating of dental sealant material to the exposed surfaces of the preformed plastic facing and the tooth enamel adjacent the marginal edges of the facing. The outer coating 30 of dental sealant material then may be polymerized in any suitable manner thereby achieving a completed restoration having the glossy outer appearance of the natural enamel surface of the restored tooth and having color characteristics that precisely correspond to the color characteristics of adjacent teeth.

If either the filler or sealant materials are premixed and become polymerized after a predetermined limit period of time, it will be necessary of course, to insure that the tooth restoration is properly colored, is properly emplaced and shaped before the curing or polymerization period ends. Use of such materials is within the spirit and scope of the present invention.

The preformed plastic facing or lamination that is to be applied to the teeth during restoration according to the method set forth herein may conveniently take any suitable form that is suitable for tooth restoration. It has been found through initial tests that a plastic material such as fully polymerized, preformed methyl methacrylate is a suitable material for tooth restoration in accordance with the teachings of the present invention. Methyl methacrylate is utilized presently in the manufacture of denture teeth and therefore corresponds very closely to the appearance and functional capabilities of natural teeth. It is envisioned that the plastic facings may be premanufactured according to various shapes, forms, colors, contour and the type of restoration desired, whether the restoration be of complete crown coverage or whether the restoration be of minimal nature such as for restoring a fracture of an incisal edge of a tooth. Plastic facings or laminations may also be provided for restoration of proximal caries. In most cases the marginal edges of the preformed plastic facings would be of knife edged configuration in order to establish a smooth contiguous surface of the joint between the enamel and the laminant facing.

The plastic facings, if desired, may be composed of very thin and flexible material that may be readily molded by application of mechanical pressure thereby causing the flexible facing to conform to the tooth surface that is to be restored. For example, it may be desirable to provide a flexible and moldable plastic facing that may be molded to conform to selected surfaces of the tooth. For example, a thin and flexible facing may cover the labial surface of the tooth and may cover one or more of the proximal edges. After applying the bonding agent to the tooth surface or to the facing, the facing may simply be emplaced and formed to conform to the configuration of the tooth. The bonding agent may then be selectively polymerized by application of ultra-violet light or by any other suitable means to achieve a proper bond between the facing and the tooth. Also, if desired, the facing and the etched surface of the tooth, may be provided with a thin coating of dental sealant that is allowed to harden in place either responsive to application of ultra-violet light or by any other suitable means of activation.

Figure 3:
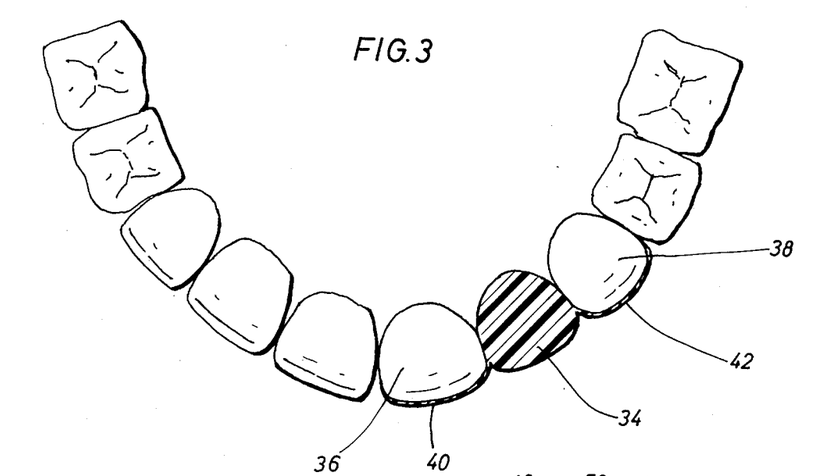
FIG. 3 is a view showing the upper teeth of a patient and depicting a dental bridge prothesis including lamina preparation of teeth that support the bridge prothesis in operative position.
Figure 4:
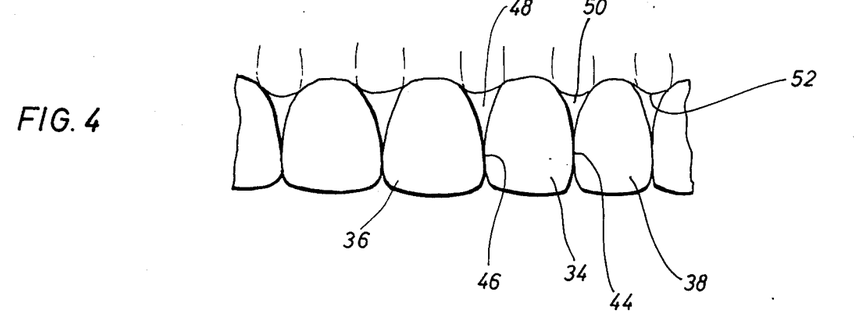
FIG. 4 is a partial elevational view of the bridge work prothesis illustrated in FIG. 3 illustrating the outward appearance of a completed bridge installation.

With reference now to FIGS. 3 and 4, in accordance with the teachings of the present invention, simple and efficient bridge work may be accomplished without necessitating provision of abutment crowns on abutment teeth adjacent a missing tooth opening within which a pontic is to be disposed. As illustrated in FIG. 3, a number of permanent teeth of a patient are depicted pictorially and a pontic 34 is substituted for a missing natural tooth. The pontic 34 is shown to be disposed between abutment teeth 36 and 38. As was mentioned hereinabove, ordinarily it is necessary, in order to support the pontic 34 in place between the abutment teeth, to provide the abutment teeth with abutment or bridge support crowns. In order to accomplish this, the abutment teeth 36 and 38 must ordinarily be reshaped by grinding to prepare the teeth for reception of abutment crowns and, of course, such reshaping permanently distorts the normal configuration of the teeth.

In accordance with the present invention, it is not necessary to reshape the abutment teeth 36 and 38 or make impressions, it being only necessary to prepare the anterior enamel surface of the abutment teeth for efficient bonding of bridge support laminations thereto. In accordance with the present invention, the pontic 34 will be formed integrally with or connected to support facing elements 40 and 42, the inner surface of which may be prepared in the same manner as discussed above in connection with preparation of the plastic facing 18 depicted in FIG. 1.

After application and polymerization of the coating of sealant to both the inside surfaces of the plastic laminar facings 40 and 42, the labial surfaces of the abutment teeth 36 and 38 may be etched with a solution of phosphoric acid or with any other suitable etching material that provides a microporous enamel surface on the abutment teeth. A coating of dental sealant may then be applied to the abutment teeth and may be subsequently polymerized. Dental filler material then may be applied either to the inside surfaces of the laminar support facings 40 and 42 or to the prepared and coated labial surfaces of the abutment teeth 36 and 38 and the pontic may then be positioned by positioning of the laminar facings 40 and 42 into intimate engaging assembly with the prepared surfaces of the abutment teeth 36 and 38. Sufficient pressure is then applied to the facings 40 and 42 to squeeze out excess dental filler material. A portion of the excess dental material is then molded about the joint created between the marginal edges of the respective facings and the prepared and coated enamel surfaces of the abutment teeth to provide a smooth contiguous surface at the joint.

After the pontic and the facings have been emplaced in the manner illustrated in FIGS. 3 and 4, the bridge work will have its final appearance and can be inspected both by the patient and by the dentist for determination if the appearance is cosmetically pleasing. After acceptance, the dental filler material then may be selectively polymerized in any suitable manner, such as by application of ultra-violet light, for example, thereby completing the bond between the facing and the tooth and ensuring that all voids that might exist between the facing and the adjacent abutment teeth are completely filled with dental filler material. After hardening of the dental filler material, desirable portions of the abutment teeth, facings and perhaps also the pontic may be lightly sanded or abraded with pumice to eliminate any irregularities in the exposed surfaces of the facings, the abutment teeth and the pontic and to prepare these surfaces for a coating of dental sealant material that is subsequently applied. The dental sealer material, after being applied will have a very glossy finish and when subsequently polymerized, such as by application of ultra-violet light thereto, will provide a bridge work that conforms as precisely as possible to the appearance of the patient's other teeth, if in fact such conformance is indeed desirable. Where the remaining teeth of the patient are discolored or cariously involved, it may be appropriate to also provide certain ones of the patient's teeth with laminar facings as discussed above in connection with FIG. 1 for enhancing the cosmetic appearance of the patient's teeth.

Referring particularly to FIG. 4, the pontic 34 will be physically connected or formed integrally with the adjacent facings 36 and 38 at the typical tooth contact areas 44 and 46. The anterior portions of the pontic and the adjacent facings will be of such configuration that the appearance of tooth separation will be given. The anterior facing and pontic structure will make effective use of shadows to enhance the appearance of tooth separation and embrasures 48 and 50 will appear between the facings and pontic and below the gum line 52. The bridge work prothesis, therefore, will have a natural appearance and it will not be necessary to modify the abutment teeth by crowning in order to provide proper support for the pontic. If it subsequently becomes desirable to remove the pontic, this may be done very simply and efficiently and the abutment teeth 36 and 38 may, if desired, be returned to the original condition thereof simply by effective removal of the facing material therefrom. If desired, the facing material may simply be removed by grinding and polishing thereby exposing the original enamel surface of the abutment teeth.

Figure 5:
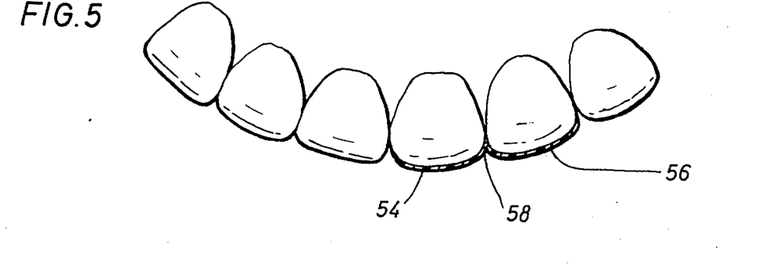
FIG. 5 is an end view of the upper incisor teeth of a patient illustrating periodontal splinting of the patient's teeth and showing the relationship of the laminar splint structure to the tooth structure of the patient's teeth.

With reference now to FIG. 5, it may be desirable to establish periodontic splinting between one or more teeth, if a tooth needs to be physically supported by another tooth. Ordinarily, when periodontically involved teeth are splinted together, it is necessary to provide both of the teeth with appropriate splinting crowns and to secure the crowns together by appropriate bonding or by other physical means. FIG. 5 discloses a pair of teeth that have been splinted together by means of laminar plastic facings that are either integrally formed or bonded together at the contact points of the teeth. Here again, the facings and the teeth to be splinted will be prepared by acid etching and coating in the same manner as discussed above in connection with FIG. 1. The plastic laminar facings 54 and 56, which are joined together at the contact point 58, are applied to the teeth with dental filler material and dental sealant in the same manner as discussed above. The material from which the facings are composed may be appropriately colored to match the adjacent teeth or may be colored as desired for pleasing cosmetic appearance. Moreover, it is not necessary to grind away the major portion of each of the teeth in order to provide splinting crowns that will secure the teeth together. In the event it is subsequently desirable to eliminate the physical support between the teeth it may be simply desirable to separate them at the contact points or in the alternative, the facing material may be removed from the teeth in any suitable manner thereby exposing the original enamel surface of the teeth.

FIGS. 2a, 2b, 2c and 2d illustrate a few of the many possible tooth restorations that are possible according to the teachings of the present invention. For example, in FIG. 2a the tooth has a fractured incisal edge, as shown in broken line. The facing applied to the labial surface of the tooth would therefore be provided with a thin labial portion covering the labial surface of the tooth and a relatively thick incisal portion would be formed integrally with the thin labial portion. The thin labial portion, in addition to covering the labial surface of the tooth and providing a pleasing cosmetic appearance thereto, will also lend strength to the labial portion of the restoration.

Figure 2A:
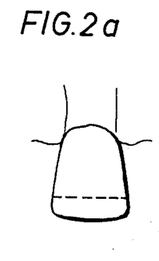
FIGS. 2A – 2D are illustrations of some of the various tooth restorations that are possible through employment of the present invention.
Figure 2B:
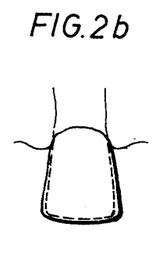
Figure 2C:
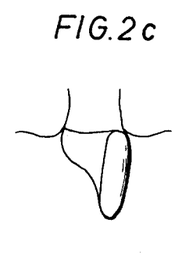

FIG. 2b depicts a tooth wherein the restoration facing includes a pair of proximal portions and an incisal portion formed integrally with a thin labial portion thereby providing proximal restoration such as would be required in the event of proximal caries. The laminar facing, in this case, will be provided with a pair of proximal portions that may both be utilized, if desirable. One of the proximal portions may be readily removed from the facing in the event only one proximal portion is desired. FIG. 2c illustrates a tooth in side view, being provided with a facing having a proximal edge portion.

Figure 2D:
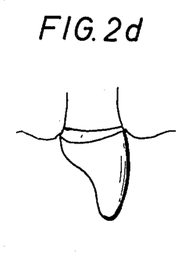

FIG. 2d shows a tooth restoration wherein the tooth is fully covered with a thin crown overlay covering the labial, incisal, proximal and lingual portions of the tooth.

It is practical to assume that cosmetic facings and plastic tooth restorations may become unsatisfactory in appearance or function after a logical period of effective use. It is also logical to assume that in a small number of cases the plastic facings or restorations may become chipped, broken, worn or detached and may need replacement. When replacement is necessary, it is simply appropriate to restore the tooth involved to the original form thereof by removal of the plastic material and thereby exposing the original enamel surface of the tooth. The process for installation of cosmetic facings and plastic restorations may simply be repeated without any structural damage to the tooth that is treated in this manner. It may be desirable to remove only part of the facing material to accomplish restoration because a plastic to plastic bond may be readily accomplished. Restoration of fractured, cariously involved or badly discolored teeth may be accomplished at minimal cost through employment of low cost materials and through conservation of dental chair time for such treatment. Through employment of the invention in practice, dental bridge work and splinting of periodontically involved teeth may also be effectively accomplished at very low cost. Moreover, it will not be necessary to alter abutment teeth or to provide crowns for periodontic splinting because the facing material itself will be of sufficient structural integrity for support of pontics and for the establishment of supporting connections between splinted teeth. One of the most important aspects of the present invention is the fact that there is no need whatever for permanently altering the physical structure of teeth either for the accomplishment of cosmetic facing or for preparation of support crowns as in the case of bridge work or periodontic splinting and the teeth may be returned to their original condition simply by removal of the facing material therefrom.

Where the teeth of a patient have become severely discolored or cariously involved such as frequently occurs when a patient lives in certain parts of the world, the teeth can be treated very simply and efficiently and at minimum cost in order to provide the teeth with a pleasing cosmetic appearance. During the process of installation of facings for cosmetic appearance, after the facings have been attached to the teeth and before the bonding material has become polymerized, the facings may be inspected for cosmetic appearance and if unacceptable, may be simply and efficiently removed and other facings may be substituted therefor. The plastic facings both for cosmetic improvement of the teeth and for restoration of fractures or carious deformation may be readily accomplished without necessitating the use of anesthesia to prepare the patient for treatment.

It is therefore apparent that the present invention is one well adapted to attain all of the objects and advantages hereinabove set forth, together with other advantages which will become obvious and inherent from a description of the method and materials utilized according to the teachings of the invention. It will be understood that certain combinations and subcombinations are of utility and may be employed without reference to other features and subcombinations. This is contemplated by and is within the scope of the present invention.

As many possible embodiments may be made of this invention without departing from the spirit or scope thereof, it is to be understood that all matters hereinabove set forth or shown in the accompanying drawings are to be interpreted as illustrative and not in a limiting sense.

Having thus fully described my invention in detail, I claim:

1. A laminar tooth facing formed of restoration material and adapted to be bonded to the enamel surface of a patient's natural tooth to provide a thin restorative covering for the labial proximal and incisal surfaces of the patient's tooth, said facing comprising:

a thin sheet-like body of preformed dental restoration material having a substantially uniform thickness, said body being preformed to define a concave lingual surface that conforms generally to the configuration of desirable portions of the natural tooth to which it is to be bonded and to define at least one proximal surface conforming to the configuration of the outer enamel surface of said tooth, said body being formed to define knife edges that engage the enamel surface of said tooth, said body being of such color as to provide a completed tooth restoration of pleasing cosmetic appearance.

2. A laminar tooth facing as recited in claim 1, wherein:
said body of tooth restoration material is thin and flexible and readily moldable to conform to desired portions of the enamel surface of the tooth being restored.

3. A laminar tooth facing as recited in claim 1, wherein:
said body of tooth restoration material is composed of plastic material and
said thin portion adapted to cover substantially all of the labial surface of the tooth to which it is to be bonded, at least some of the edges of said thin portion being tapered to define knife edges that engage the enamel surface of said tooth; and
a portion integral with said thin portion that conforms to any tooth deformity and restores the tooth to the normal configuration thereof.

4. A laminar tooth facing as recited in claim 3, wherein said body of plastic material includes:
at least one lingual portion formed integral with said thin portion and being adapted for bonding to the enamel surface of said tooth to be restored at at least one of the lingual edges of said tooth.

5. A laminar tooth restoration element adapted to be bonded to the enamel surface of at least one of a patient's teeth, said tooth restoration element comprising:
a body of dental restoration material, said body having portions of the outer enamel surface of the teeth to which it is to be bonded, said body being of such color to provide a completed tooth restoration of pleasing cosmetic appearance, said body defining
a pair of abutment facings adapted to be bonded to the labial surfaces of abutment teeth disposed on either side of a tooth space created by a missing tooth or teeth; and
a pontic being connected to each of said abutment facings and being supported by said abutment facings within said space.

6. A laminar tooth restoration element as recited in claim 5, wherein:
said pontic is formed integrally with said abutment facings.

7. A laminar tooth restoration element adapted to be bonded to the enamel surface of at least one of a patient's teeth, said tooth restoration element comprising:
a body of dental restoration material, said body being preformed to conform generally to desirable portions of the outer enamel surface of the teeth to which it is to be bonded, said body being of such color to provide a completed tooth restoration of pleasing cosmetic appearance, said body defining at least two periodontic splinting facings adapted to be bonded to the labial surfaces of adjacent teeth, said periodontic splinting facings being disposed in rigid assembly for securing a plurality of teeth to be periodontically splinted in rigid relationship.

8. A method of restoring teeth of a patient that have become badly discolored, fractured or cariously involved, said method comprising the steps of:
etching appropriate portions of the enamel of the teeth of the patient with an acid solution to provide surface irregularities in the enamel;
providing laminar facings for the teeth to be restored, which facings conform to the configuration of the surfaces of the teeth to be restored;
disposing between the etched surface of the enamel of the teeth and the laminar facings a quantity of bonding agent;
applying mechanical pressure to the laminar facings to expell excess bonding agent from between the laminar facings and the etched surface of the enamel;
forming a small quantity of bonding agent about the joint established between the marginal edges of the laminar facings and the enamel surface of the teeth;
allowing the bonding agent to cure in place; and
finishing the exterior surface of the laminar tooth restoration to yield a smooth exterior tooth restoration surface.

9. A method of restoring teeth as recited in claim 8, including the method steps of:
coating the etched surfaces of the teeth and the interior surfaces of the laminar facings with dental sealant and allowing the sealant to harden; and
disposing a quantity of dental filler material between the hardened coated surfaces of the teeth and laminar facings and allowing the dental filler material to harden in place.

10. A method of restoring teeth as recited in claim 8, wherein:
said bonding agent comprises:
a type of bonding agent that is produced by the reaction product of Bisphenol A and Glycidyl Methacrylate, said bonding agent being activated by Bensoin methyl ether and becoming polymerized following exposure to ultra-violet light.

11. A method of restoring teeth as recited in claim 8, wherein said bonding agent comprises:
a two part bonding agent that polymerizes within a predetermined period of time after said two parts are mixed.

12. A method of tooth restoration comprising the method steps of:
etching appropriate surfaces of the enamel of the teeth to be restored with an acid material;
coating appropriate surfaces of the teeth with dental coating material that penetrates the interstices of the etched enamel;
allowing said coating material to harden;
providing a plastic facing that covers said appropriate surfaces of said teeth, said plastic facing being composed of preformed fully cured material;
coating the inside surfaces of said plastic facing with said dental coating material;
allowing said dental coating material to harden;
applying a quantity of dental filler material between said appropriate surfaces of the teeth and to the inside surface of said plastic facing;
forcing said facing into assembly with said appropriate coated surfaces of said teeth with sufficient mechanical pressure to expel any excess of said dental filler material from between said facing and said teeth;

shaping dental filler material about the joint established between the marginal edges of the plastic facing and the coated enamel surface of said tooth;

allowing said dental filler material to harden;

applying a coating of dental coating material to the exterior of said facing, said coating covering the joint between the marginal edges of said facing and the coated enamel surface of said tooth; and allowing said coating to harden.

13. A method of tooth restoration as recited in claim 12, wherein:
said dental coating material is controllably polymerized in place following application thereof.

14. A method of tooth restoration as recited in claim 12, wherein:
said dental coating material is controllably polymerized in place following application thereof; and
said dental filler material is controllably polymerized in place following application thereof.

15. A method of tooth restoration as recited in claim 12, wherein;
said dental sealant material and said dental filler material are of a type that is produced by the reaction product of Bisphenol A and Glycidyl Methacrylate, said dental sealant and dental filler materials being activated by Benzoin methyl ether and becoming polymerized following exposure to ultra-violet light.

16. A method of tooth restoration as recited in claim 12, wherein said facing is formed of flexible plastic material and said method includes:
forming said facing to the external configuration of selected surface areas of said tooth prior to allowing said dental filler material to harden, whereby said facing will retain its formed configuration in addition to becoming bonded to the structure of the tooth.

17. Dental bridge work apparatus comprising:
a pontic formed of dental restoration material and adapted to be disposed in the space defined between abutment teeth; and
at least a pair of laminar facings being connected one on either side of said pontic and supporting said pontic, said facings conforming to at least the labial surfaces of said abutment teeth.

18. Dental bridge work apparatus as recited in claim 17, including:
a bonding agent for securing said facings to the enamel surface of said teeth.

19. Dental bridge work apparatus as recited in claim 17, including:
a thin layer of dental sealant material being applied to etched enamel surfaces of said teeth and to the inside surfaces of said facings and allowed to harden; and
a quantity of dental filler material being disposed between said coated surfaces of said enamel and said facings and allowed to harden.

20. Dental bridge work apparatus as recited in claim 19, including:
a thin coating of dental sealant material being disposed about selected exposed surfaces of said facings and said teeth and allowed to harden.

21. Dental bridge work apparatus as recited in claim 20, wherein said dental sealant material and said dental filler material comprise:
a reaction product of Bisphenol A and Glycidyl Methacrylate, said reaction product being activated by Benzoin methyl ether and becoming polymerized following exposure to ultra-violet light.

22. Dental bridge work apparatus as recited in claim 15, wherein said laminar facings are composed of thin flexible plastic material that is readily moldable to the surface configuration of the abutment teeth.

23. A periodontic splint, comprising:
a plurality of laminar facings composed of preformed fully curved dental restoration material, said facings adapted to cover at least the labial surfaces of the teeth to be periodontically splinted,
means securing at least a part of the proximal edges of said facings in rigid assembly; and
means for bonding said plurality of laminar facings to the enamel of said teeth.

24. A periodontic splint as recited in claim 23, wherein said means for bonding said facings to said enamel comprise:
a coating of dental sealant material being applied to the juxtaposed surfaces of said enamel and said facings and allowed to harden in place; and
a quantity of dental filler material being disposed between the coated surfaces of said enamel and said facings and filling the voids therebetween, said dental filler material being allowed to harden in place.

25. A periodontic splint as recited in claim 23, wherein:
said facings are of sufficient thinness and flexibility as to be readily moldable to the physical configuration of selected surfaces of the enamel of the teeth.

26. For use with the natural tooth of a dental patient, a thin laminar facing formed of tooth restoration material for covering the labial, proximal and incisal surfaces of the patient's tooth, said laminer facing comprising:
a thin curved preformed body of tooth restoration material, having a substantially uniform thickness, said body having a thin labial portion of convex configuration defining a proximal surface of concave configuration, said proximal surface generally conforming to the configuration of the labial surface of said tooth, at least some of the edges of said body of tooth restoration material being tapered to define knife edges that engage the enamel surface of said tooth; and
means for securing said preformed body of tooth restoration material to said natural tooth.

27. The combination as recited in claim 26, wherein:
said preformed body of tooth restoration material is flexible and is moldable to the configuration of the enamel surface of said tooth.

* * * * *

REEXAMINATION CERTIFICATE (1316th)
United States Patent [19]

Faunce

[11] B1 3,986,261
[45] Certificate Issued Jul. 3, 1990

[54] METHOD AND APPARATUS FOR RESTORING BADLY DISCOLORED, FRACTURED OR CARIOUSLY INVOLVED TEETH

[75] Inventor: Frank R. Faunce, 1307 Wilcrest Dr., Apt. 237, Houston, Tex. 77025

[73] Assignees: Frank R. Faunce; Tae Deborah Harrell Z. Browning; James R. Harris; Scott T. Cook; Edward F. Barker

Reexamination Request:
No. 90/001,629, Oct. 31, 1988

Reexamination Certificate for:
Patent No.: 3,986,261
Issued: Oct. 19, 1976
Appl. No.: 421,846
Filed: Dec. 5, 1973

[51] Int. Cl.$^5$ .............................................. A61C 5/00
[52] U.S. Cl. ................................................. 433/217.1
[58] Field of Search ................... 433/217.1, 218, 215, 433/180

[56] References Cited

U.S. PATENT DOCUMENTS

| | | | |
|---|---|---|---|
| 3,004,343 | 10/1961 | Rydin | 433/203.1 |
| 3,066,112 | 11/1962 | Bowen | 526/279 |
| 3,469,317 | 9/1969 | Jarby | 433/217.1 |
| 3,503,128 | 3/1970 | Boyd et al. | 433/228.1 |
| 3,763,564 | 10/1973 | Petrelli et al. | 32/2 |
| 3,895,445 | 7/1975 | Silverman et al. | 433/9 |

FOREIGN PATENT DOCUMENTS

| | | | |
|---|---|---|---|
| 1122220 | 1/1962 | Fed. Rep. of Germany | 433/218 |
| 2008781 | 12/1971 | Fed. Rep. of Germany | 433/218 |

OTHER PUBLICATIONS

"The Elimination of All Conspicuous Cavities and Fillings in the Anterior Teeth", by C. H. Land, *The Dental Summary*, 1908, pp. 564-589.
"Porcelain Dental Art" by Charles H. Land, *The Dental Cosmos*, vol. XLV, 1903, pp. 615-620.
"The Practical Adjustment of Dental Porcelain as Applied to Operative Dentistry" by Dr. C. H. Land, *Dominion Dental Journal*, 1907, pp. 5-11.
"Building Mouth Personality" by Charles Leland Pincus, *Journal of California State Dental Association*, Jul.-Aug., 1938, pp. 125-129.
"A Simple Method of Increasing the Adhesion of Acrylic Filling Materials to Enamel Surfaces" by Dr. Michael G. Buonocore, *Journal of Dental Research*, Dec. 1955, pp. 849-853.
"Attachment of Resin Restorations to Acid Pretreated Enamel", by Harold R. Laswell et al., *JADA*, vol. 82, Mar. 1971, pp. 558-653.
"Effect of Conditioning the Enamel Surface With Phosphoric Acid" by D. H. Retief, *Journal Dental Research*, Mar.-Apr. 1971, pp. 333-341.
"Acrylic Adhesives for Bonding Attachments to Tooth Surfaces", by George V. Newman et al., *Adhesives*, vol. 38, No. 1, Jan. 1968, pp. 12-18.

*Primary Examiner*—John J. Wilson

[57] ABSTRACT

A method and apparatus for restoring badly discolored, fractured or cariously involved teeth by etching desirable parts of the enamel surface of the tooth and by adhering to the tooth a properly colored polymerized, preformed plastic facing that has a pleasing cosmetic appearance or corresponds to the coloring of adjacent teeth as desired. The etched surface of the tooth, the inside surface of the facing material and the exposed surface of the facing material including the joint between the facing material and the enamel of the tooth are coated with a controlled curing dental adhesive material that may be selectively cured in place, such as by ultra-violet activation. The voids between the tooth and the facing material may be filled with a controlled curing dental filler material that may also be molded about the joint between the tooth enamel and the facing material. The dental filler material may also be of the type that is cured in place such as by curing following ultra-violet activation. Facings bonded to the enamel of abutment teeth may be employed for support of pontics without necessitating preparation of abutment teeth with bridgework support crowns. Connected facings may also be employed for periodontic splinting.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 8-16 is confirmed.

Claims 1, 3, 5, 7, 17, 18, 22, 23 and 26 are determined to be patentable as amended.

Claims 2, 4, 6, 19-21, 24, 25 and 27, dependent on an amended claim, are determined to be patentable.

1. A laminar tooth facing *for a single tooth, said facing being* formed of restoration material and adapted to *intimately fit the enamel surface of a patient's tooth and to* be bonded to the enamel surface of a patient's natural tooth to provide a thin restorative covering for the labial proximal and incisal surfaces of the patient's tooth, said facing comprising:
   a thin sheet-like body of preformed dental restoration material having a substantially uniform thickness, said body being preformed to define a concave lingual surface that *intimately* conforms [generally] to the configuration of [desirable] *the labial enamel surface* portions of the natural tooth to which it is to be bonded and to define at least one proximal surface *intimately* conforming to the configuration of the outer enamel surface of said tooth, said body being formed to define [knife edges] *a sharp marginal edge* that [engage] *engages and establishes a contiguous margin with* the enamel surface of said tooth, said body being of such color as to provide a completed tooth restoration of pleasing cosmetic appearance.

3. A laminar tooth facing as recited in claim 1, wherein:
   said body of tooth restoration material is composed of plastic material [and];
   said thin portion adapted to cover substantially all of the labial surface of the tooth to which it is to be bonded, at least some of the edges of said thin portion being tapered to define [knife] *sharp* edges that engage the enamel surface of said tooth; and
   a portion integral with said thin portion that conforms to any tooth deformity and restores the tooth to the normal configuration thereof.

5. A laminar tooth restoration element adapted to *intimately fit and to* be bonded to the enamel surface of at least one of a patient's teeth *and to form a thin restorative covering for the labial, proximal and incisal surfaces thereof,* said tooth restoration element comprising:
   a body of dental restoration material, said body having portions of the outer enamel surface of the teeth to which it is to be bonded, said body being of such color to provide a completed tooth restoration of pleasing cosmetic appearance, said body defining a pair of abutment facings *each comprising a thin sheet-like body of preformed dental restoration material having a substantially uniform thickness and defining a concave lingual surface* adapted to *intimately fit and to* be bonded to the labial *enamel* surfaces of abutment teeth disposed on either side of a tooth space created by a missing tooth or teeth, *said abutment facings each defining sharp marginal edges engaging and forming a contiguous margin with the enamel surfaces of said abutment teeth*; and
   a pontic being connected to each of said abutment facings and being supported by said abutment facings within said space.

7. A laminar tooth restoration element *being* adapted to *intimately fit and* to be bonded to the enamel surface of at least one of a patient's teeth *to provide a thin restorative covering therefor*, said tooth restoration element comprising:
   *a plurality of interconnected tooth facings each comprising* a *thin sheet-like* body of dental restoration material *having a substantially uniform thickness*, said body being preformed to conform [generally] *intimately* to desirable portions of the outer enamel surface of the [teeth] *tooth* to which it is to be bonded, said body being of such color to provide a completed tooth restoration of pleasing cosmetic appearance, said body defining at least two periodontic splinting facings *each* adapted to *intimately fit and to* be bonded to the labial *enamel* surfaces of adjacent teeth *and defining sharp marginal edges engaging and forming a contiguous margin with the enamel surfaces of each of said adjacent teeth*, said periodontic splinting facings being disposed in rigid assembly for securing a plurality of teeth to be periodontically splinted in rigid relationship.

17. Dental bridge work apparatus comprising:
    a pontic formed of dental restoration material and adapted to be disposed in the space defined between abutment teeth; and
    at least a pair of laminar facings *each for a single tooth and* being connected one on either side of said pontic and supporting said pontic, said *laminar* facings *each* being adapted to intimately fit the enamel surface *of a patient's tooth and defining a thin sheet-like body formed of restoration material and having a substantially uniform thickness, said laminar facing* being preformed to define a concave lingual surface conforming to at least the labial surfaces of said abutment teeth *and forming sharp marginal edges that engage and form a contiguous margin with the enamel surfaces of said abutment teeth*.

18. Dental bridge work apparatus as recited in claim 17, including:
    a *polymer* bonding agent for [securing] *bonding* said *laminar* facings to the *respective* enamel [surface] *surfaces* of said *abutment* teeth.

22. Dental bridge work apparatus as recited in claim [15] *17*, wherein said laminar facings are composed of thin flexible plastic material that is readily moldable to the surface configuration of the abutment teeth.

23. A periodontic splint, comprising:
    a plurality of laminar facings *each for a single tooth and being* composed of preformed fully [curved] *cured* dental restoration material *and each being of substantially uniform thickness and being adapted to intimately fit and to be bonded to the enamel surface of the respective tooth*, said facings adapted to [cover] *provide a thin restorative covering for* at least the labial *enamel* surfaces of the teeth to be periodontically splinted *and forming sharp marginal edges that engage and form a contiguous margin with the enamel surfaces of said single teeth,* means securing at least a part of the proximal edges of said facings in rigid assembly; and means for bonding said plurality of laminar facings to the enamel of said teeth.

26. For use with [the] *a single* natural tooth of a dental patient, a thin laminar facing formed of tooth restoration material for covering the labial, proximal and incisal *enamel* surfaces of the patient's tooth *and adapted to intimately fit the enamel surface of a patient's tooth and forming a permanent restoration therewith*, said [laminer] *laminar* facing comprising:

a thin curved preformed body of tooth restoration material, having a substantially uniform thickness *and forming marginal edges*, said body having a thin labial portion of convex configuration *and* defining [a proximal] *an inner* surface of concave configuration, said [proximal] *inner* surface [generally] conforming *intimately* to the configuration of the labial *enamel* surface of said tooth, at least some of the *marginal* edges of said body of tooth restoration material being tapered to define [knife] *sharp* edges that engage *and form a contiguous margin with* the enamel surface of said tooth; and means for securing said preformed body of tooth restoration material to *the enamel surface of* said natural tooth.

* * * * *